US009037204B2

(12) United States Patent
Schlottau (10) Patent No.: US 9,037,204 B2
(45) Date of Patent: May 19, 2015

(54) FILTERED DETECTOR ARRAY FOR OPTICAL PATIENT SENSORS

(75) Inventor: Friso Schlottau, Lyons, CO (US)

(73) Assignee: COVIDIEN LP, Mansfield, MA (US)

( * ) Notice: Subject to any disclaimer, the term of this patent is extended or adjusted under 35 U.S.C. 154(b) by 608 days.

(21) Appl. No.: 13/226,637

(22) Filed: Sep. 7, 2011

(65) Prior Publication Data

US 2013/0060104 A1 Mar. 7, 2013

(51) Int. Cl.
*A61B 5/1455* (2006.01)

(52) U.S. Cl.
CPC ......... *A61B 5/14558* (2013.01); *A61B 5/14552* (2013.01)

(58) Field of Classification Search
USPC .................................................. 600/310–344
See application file for complete search history.

(56) References Cited

U.S. PATENT DOCUMENTS

| | | | |
|---|---|---|---|
| 5,299,570 A | | 4/1994 | Hatschek |
| 5,553,613 A | * | 9/1996 | Parker ........................... 600/316 |
| 5,922,607 A | | 7/1999 | Bernreuter |
| 5,965,875 A | | 10/1999 | Merrill |
| 5,983,122 A | * | 11/1999 | Jarman et al. .................. 600/323 |
| 6,044,285 A | * | 3/2000 | Chaiken et al. ............... 600/316 |
| 6,078,833 A | | 6/2000 | Hueber |
| 6,477,393 B1 | * | 11/2002 | Chou ............................ 600/316 |
| 6,587,703 B2 | | 7/2003 | Cheng et al. |
| 6,597,931 B1 | | 7/2003 | Cheng et al. |
| 6,620,643 B1 | * | 9/2003 | Koike ............................. 438/30 |
| 6,671,526 B1 | | 12/2003 | Aoyagi et al. |
| 6,801,799 B2 | | 10/2004 | Mendelson |
| 7,027,849 B2 | | 4/2006 | Al-Ali |
| 7,391,008 B2 | * | 6/2008 | Fouquet et al. ............... 250/226 |
| 2002/0042558 A1 | | 4/2002 | Mendelson |
| 2003/0144583 A1 | * | 7/2003 | Cheng et al. .................. 600/322 |
| 2006/0020181 A1 | | 1/2006 | Schmitt |
| 2006/0084864 A1 | | 4/2006 | Schmitt et al. |
| 2006/0211923 A1 | | 9/2006 | Al-Ali et al. |

(Continued)

FOREIGN PATENT DOCUMENTS

| | | |
|---|---|---|
| EP | 0630203 B1 | 7/2002 |
| FR | 2685865 | 7/1993 |

(Continued)

OTHER PUBLICATIONS

U.S. Appl. No. 13/077,105, filed Mar. 31, 2011, David Trumble.

(Continued)

*Primary Examiner* — Eric Winakur
*Assistant Examiner* — Marjan Fardanesh
(74) *Attorney, Agent, or Firm* — Fletcher Yoder PC (57) ABSTRACT

The present embodiments relate generally to patient monitoring system and, more particularly, to optical patient monitoring systems. In an embodiment, a physiological sensor includes a broadband emitter configured to emit two or more wavelengths of light into the tissue of a patient. The sensor also includes a charge coupled device (CCD) or complementary metal-oxide semiconductor (CMOS) photodetector array comprising a plurality of photodetectors. Each photodetector in the photodetector array is configured to receive the light from the tissue of the patient and to produce a corresponding output signal. Additionally, the sensor also includes one or more filter layers disposed on the plurality of photodetectors. The filter layers are configured to only allow light of particular wavelengths, polarizations, or both, to be received by each of the plurality of photodetectors.

18 Claims, 6 Drawing Sheets

(56) References Cited

U.S. PATENT DOCUMENTS

| | | | |
|---|---|---|---|
| 2006/0211924 A1 | 9/2006 | Dalke et al. | |
| 2007/0241260 A1* | 10/2007 | Jaeger et al. | 250/214.1 |
| 2008/0081972 A1 | 4/2008 | Debreczeny | |
| 2008/0139906 A1 | 6/2008 | Bussek | |
| 2008/0171926 A1 | 7/2008 | Sola I Caros et al. | |
| 2008/0221411 A1* | 9/2008 | Hausmann et al. | 600/310 |
| 2008/0234560 A1 | 9/2008 | Nomoto et al. | |
| 2009/0326347 A1 | 12/2009 | Scharf | |
| 2011/0046464 A1 | 2/2011 | Debreczeny et al. | |
| 2012/0277559 A1* | 11/2012 | Kohl-Bareis et al. | 600/324 |

FOREIGN PATENT DOCUMENTS

| | | |
|---|---|---|
| JP | 2004290544 | 10/2004 |
| JP | 200675354 | 3/2006 |
| JP | 2006326153 | 12/2006 |
| WO | WO9309711 | 5/1993 |
| WO | WO9502358 | 1/1995 |
| WO | WO2005025399 A2 | 3/2005 |
| WO | WO2008134813 A1 | 11/2008 |

OTHER PUBLICATIONS

Lutter, N., et al.; "Comparison of Different Evaluation Methods for a Multi-wavelength Pulse Oximeter,"*Biomedizinische Technik*, vol. 43, 10 pages (1998).

Ikeda, Kenji, et al.; "Improvement of Photo-Electric Plethysmograph Applying Newly Developed Opto-Electronic Devices," *IEEE Tencon*, pp. 1109-1112 (1999).

Aoyagi, T., et al.; "Pulse Oximeters: background, present and future," *Neonatal Care*, vol. 13, No. 7, pp. 21-27 (2000) (Article in Japanese—contains English summary of article).

Cubeddu, Rinaldo, et al.; "Portable 8-channel time-resolved optical imager for functional studies of biological tissues," *Photon Migration, Optical Coherence Tomography, and Microscopy, Proceedings of SPIE*, vol. 4431, pp. 260-265 (2001).

Lopez-Silva, Sonnia Maria Lopez, et al.; "NIR transmittance pulse oximetry system with laser diodes," *Clinical Diagnostic Systems, Proceedings of SPIE*, vol. 4255, pp. 80-87 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Liu, Ying, et al.; "Sensor design of new type reflectance pulse oximetry," *Optics in Health Care and Biomedical Optics: Diagnostics and Treatment, Proceedings of SPIE*, vol. 4916, pp. 98-102 (2002).

Yoon, Gilwon, et al.; Multiple diagnosis based on Photoplethysmography: hematocrit, SpO2, pulse and respiration, *Optics in Health Care and Biomedical optics: Diagnostics and Treatment; Proceedings of the SPIE*, vol. 4916; pp. 185-188 (2002).

Lopez-Silva, Sonnia Maria Lopez, et al.; "Near-infrared transmittance pulse oximetry with laser diodes," *Journal of Biomedical Optic*, vol. 8, No. 3, pp. 525-533 (Jul. 2003).

Mendelson, Y., et al.; "Measurement Site and Photodetector Size Considerations in Optimizing Power Consumption of a Wearable Reflectance Pulse Oximeter," *Proceedings of the 25th Annual International conference of the IEEE EMBS*, Cancun, Mexico, 4 pages, Sep. 17-21, 2003.

Pujary, C., et al.; "Photodetector Size Considerations in the Design of a Noninvasive Reflectance Pulse Oximeter for Telemedicine Applications," *IEEE*, pp. 148-149, 2003.

Lopez-Silva, S.M., et al.; "Transmittance Photoplethysmography and Pulse Oximetry With Near Infrared Laser Diodes," *IMTC 2004—Instrumentation and Measurement Technology Conference*, Como, Italy, pp. 718-723, May 18-20, 2004.

Odagiri, Y.; "Pulse Wave Measuring Device," *Micromechatronics*, vol. 42, No. 3, pp. 6-11 (Article in Japanese—contains English summary of article) undated.

www.oceanoptics.com/Products/benchoptious_usb4.asp; (4 pages) last viewed Jan. 31, 2012.

www.taosinc.com/ProductDetails.aspx?id=9; (1 page) last viewed Jan. 31, 2012.

www.sigma-sd.com/SD1/pdf/SD1_Catalog2011_EN_MonitorRes.pdf; (2 pages) last viewed Jan. 31, 2012.

\* cited by examiner

FILTERED DETECTOR ARRAY FOR OPTICAL PATIENT SENSORS

BACKGROUND

The present disclosure relates generally to patient monitoring system and, more particularly, to optical patient monitoring systems.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors routinely desire to monitor certain physiological characteristics of their patients. Accordingly, a wide variety of systems and devices have been developed for monitoring many of these physiological characteristics. Generally, these patient monitoring systems provide doctors and other healthcare personnel with the information they need to provide the best possible healthcare for their patients. Consequently, such monitoring systems have become an indispensable part of modern medicine.

One technique for monitoring certain physiological characteristics of a patient involves emitting light into the tissue of a patient, detecting a portion of the light back from the tissue of the patient, and determining one or more physiological parameters based on the detected light. For example, using different wavelengths of light it is possible to determine the hydration level and/or the oxygen saturation of a patient. Generally, a number of different wavelengths of light may be measured in combination to determine a particular physiological parameter.

In general, the patient sensor may measure the relative contributions of the individual wavelength components of the light detected from the patient's tissue in order for the physiological parameter of the patient to be determined. For example, some patient sensors may employ a spectrometer with a diffraction grating in order to separate the incident light into its various wavelength components and determine the relative contributions of the various wavelengths present. However, spectrometers are relatively costly, sensitive to vibration and alignment issues, and may add considerable bulk to a patient monitoring system.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When multiple wavelengths of light are used in an optical patient sensor (e.g., a pulse oximetry sensor) of a patient monitoring system, the patient sensor may either include a broadband light source (e.g., a white light bulb or a phosphor-modified LED) or a number of narrowband sources (e.g., light emitting diodes (LEDs)) to emit the various wavelengths of light into the tissue of the patient. Since a number of different wavelengths of light may traverse the patient's tissue and arrive at the detector of the sensor, certain portions of the detector may selectively measure only certain wavelengths of the incident light. Accordingly, the disclosed embodiments include a charge-coupled device (CCD) or complementary metal-oxide-semiconductor (CMOS) detector array having one or more filters disposed over each photodetector element in the detector array, enabling portions of the detector array to only detect light of certain wavelengths and/or polarizations. Furthermore, the disclosed embodiments also include detector arrays having multiple layers of filters, which further restrict the wavelengths and/or polarizations of light that portions of the detector array may detect.

Generally speaking, there are numerous benefits to employing a filtered detector array in a patient monitoring system. For example, each photodetector element in the detector array, or any subgroup thereof, may be scanned to assess the quality of the signal from certain portions of the detector array. Accordingly, the patient monitoring system may ensure that the best signal from the detector array is used for calculating the physiological parameter of the patient. Additionally, when multiple portions of the detector array are configured to perform the same measurement (e.g., measure light of the same wavelength and/or polarization) at a slightly different location on the patient, the robustness of the sensor to localized issues and effects may be improved. For example, such detector arrays offer redundancy and, therefore, the portions of the detector array configured to perform the same measurement may be used for comparison such that unreasonable signals may be discarded based on the general consensus. Additionally, the filtered detector array may allow for the averaging out of local effects of the tissue. That is, if the measurement of a particular photodetector is skewed (e.g., due to the presence of a bone or a vessel in the light path between the emitter and detector), then averaging the signals from the portions of the detector array measuring the same type of light may mitigate the effect of the local tissue irregularities on the calculation of the physiological parameter of the patient. Furthermore, in such a filtered detector array, the failure of a single photodetector would not necessarily result in a failure of the sensor since one or more of photodetectors may still be functional to measure a similar light signal, albeit from a slightly different location.

Generally speaking, the disclosed embodiments improve the effectiveness of a detector array of an optical patient sensor without adding the bulk, the complexity, or the cost of a spectrometer. That is, the disclosed embodiments enable multiple portions of the detector array to detect light of a similar wavelength and/or polarization, allowing for measurements of similar light traversing different paths through the patient's tissue, increasing the robustness of the sensor. As such, by employing a filtered detector array and a broadband light source, certain disclosed patient sensor embodiments may enable the averaging out local vasculature effects, providing a better overall measurement of the patient's physiological parameter. Furthermore, by utilizing a single broadband light source rather than a number of narrowband LEDs, the disclosed embodiments may reduce the complexity and cost of the patient sensor.

Figure 1:
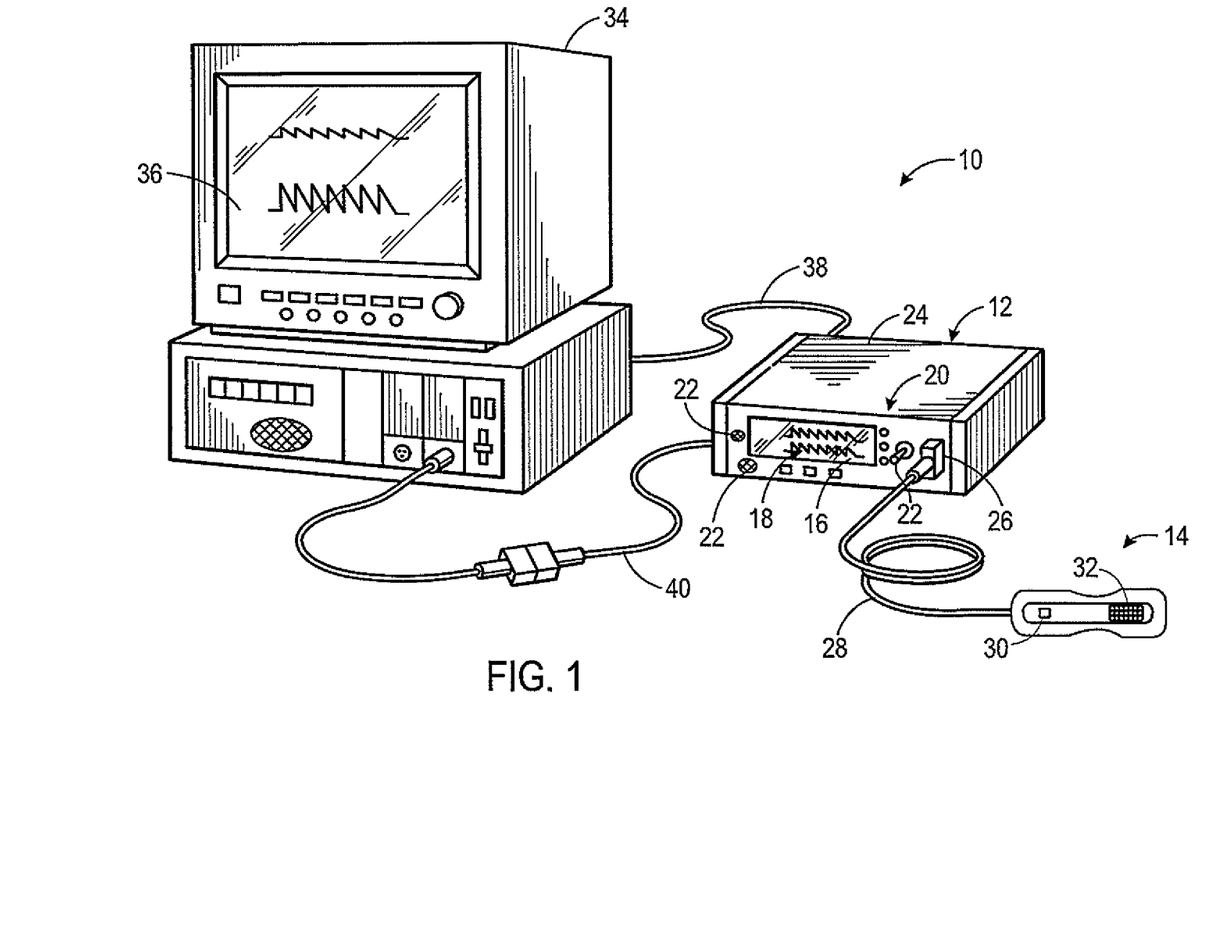
FIG. 1 illustrates a perspective view of a pulse oximeter, in accordance with an embodiment of the present disclosure.

With the foregoing in mind, FIG. 1 illustrates a perspective view of a patient monitoring system 10 that utilizes a filtered detector array to determine, one or more physiological parameters of a patient. The patient monitoring system may be a pulse oximetry monitoring system 10, which monitors the oxygen saturation level of a patient, an optical aquametry monitoring system 10, which monitors the hydration level of the patient, or both. The patient monitoring system 10 and may include a monitor 12, such as those available from Nellcor Puritan Bennett LLC, as well as a sensor 14. The monitor 12 may be configured to display measured and calculated parameters on a display 16. As illustrated, the display 16 may be integrated into the monitor 12. The display 16 may be configured to display computed physiological data including, for example, an oxygen saturation percentage (e.g., $SpO_2$ percentage), a hydration level, a pulse rate, and/or a plethysmographic waveform 18. The monitor 12 may also display information related to alarms, monitor settings, and/or signal quality via indicator lights 20. To further facilitate user input, and the monitor 12 may include a plurality of control inputs 22. The control inputs 22 may include fixed function keys, programmable function keys, a touch screen, and soft keys. The control inputs may allow the user to adjust operational parameters of the patient monitoring system 10, such as calibrating sensors or adjusting coefficients used in the calculation of the patient's physiological characteristics. The monitor 12 may also include a casing 24 that may aid in the protection of the internal elements of the monitor 12 from damage.

The monitor 12 may further include a sensor port 26. The monitor 12 may allow for connection to the patient sensor 14 via cable 28, which connects to the sensor port 26. Alternatively, in certain embodiments, a wireless transmission device may be utilized instead of (or in addition to) the cable 28.

Furthermore, the sensor 14 may be of a disposable or a non-disposable type and may include a flexible substrate to allow the sensor 14 to conform to the patient. The sensor 14 also includes an emitter 30 configured to emit a number of different wavelengths of light into the tissue of the patient and toward a filtered detector array 32, which in turn detects light passing through, reflected, or fluoresced by the patient's tissue. The patient monitor 12 may be configured to calculate physiological parameters received from the sensor 14 relating to this light detection. For example, the sensor 14 may obtain readings from a patient, which can be used by the monitor to calculate certain physiological characteristics, such as the blood-oxygen saturation of hemoglobin in arterial blood, a measure of a patient's dehydration, the volume of individual blood pulsations supplying the tissue, and/or the rate of blood pulsations corresponding to each heartbeat of a patient.

In certain circumstances, it may be useful for a medical professional to have various physiological parameters of the patient collected and displayed in one location. Accordingly, the patient monitoring system 10 may include a multi-parameter patient monitor 34, such as a computer or similar processing-relating equipment. The multi-parameter patient monitor 34 may be generally configured to calculate physiological parameters of the patient and to provide a display 36 for information from the patient monitoring system 10, in addition to other medical monitoring devices or systems. In the present context, the multi-parameter patient monitor 34 may allow a user to address the patient monitor 12, for example, to adjust operational parameters or manage alerts. Additionally, the central display 36 may allow the user to, for example, view current settings, view real-time spectra, view alarms, etc. for the patient monitoring system 10 or other connected medical monitoring devices and systems. The monitor 12 may be communicatively coupled to the multi-parameter patient monitor 34 via a cable 38 or 40 and coupled to a sensor input port or a digital communications port, respectively. In addition, the monitor 12 and/or the multi-parameter patient monitor 34 may be connected to a network to enable the sharing of information with servers or other workstations.

In general, the patient sensor 14 includes a number of components that cooperate with a number of components of the patient monitor 12 to determine one or more physiological parameters of a patient. More specifically, turning to FIG. 2, a simplified block diagram of a patient monitoring system 10 illustrates certain components of the sensor 14 and the monitor 12. The illustrated sensor 14 includes an emitter 30 and a detector array 32. The emitter 30 may be capable of emitting light of a plurality of wavelengths of light into the tissue of a patient 50 so that the physiological characteristics of the patient 50 may be determined. The light emitted by an emitter 30 may be used to measure, for example, blood oxygenation levels, pulse rate, water fractions, hematocrit, or other physiologic parameters of the patient 50. It should be understood that, as used herein, the term "light" may refer to one or more of ultrasound, radio, microwave, millimeter wave, infrared (IR), visible, ultraviolet (UV), gamma-ray or X-ray electromagnetic radiation for use with the present disclosure.

Figure 2:
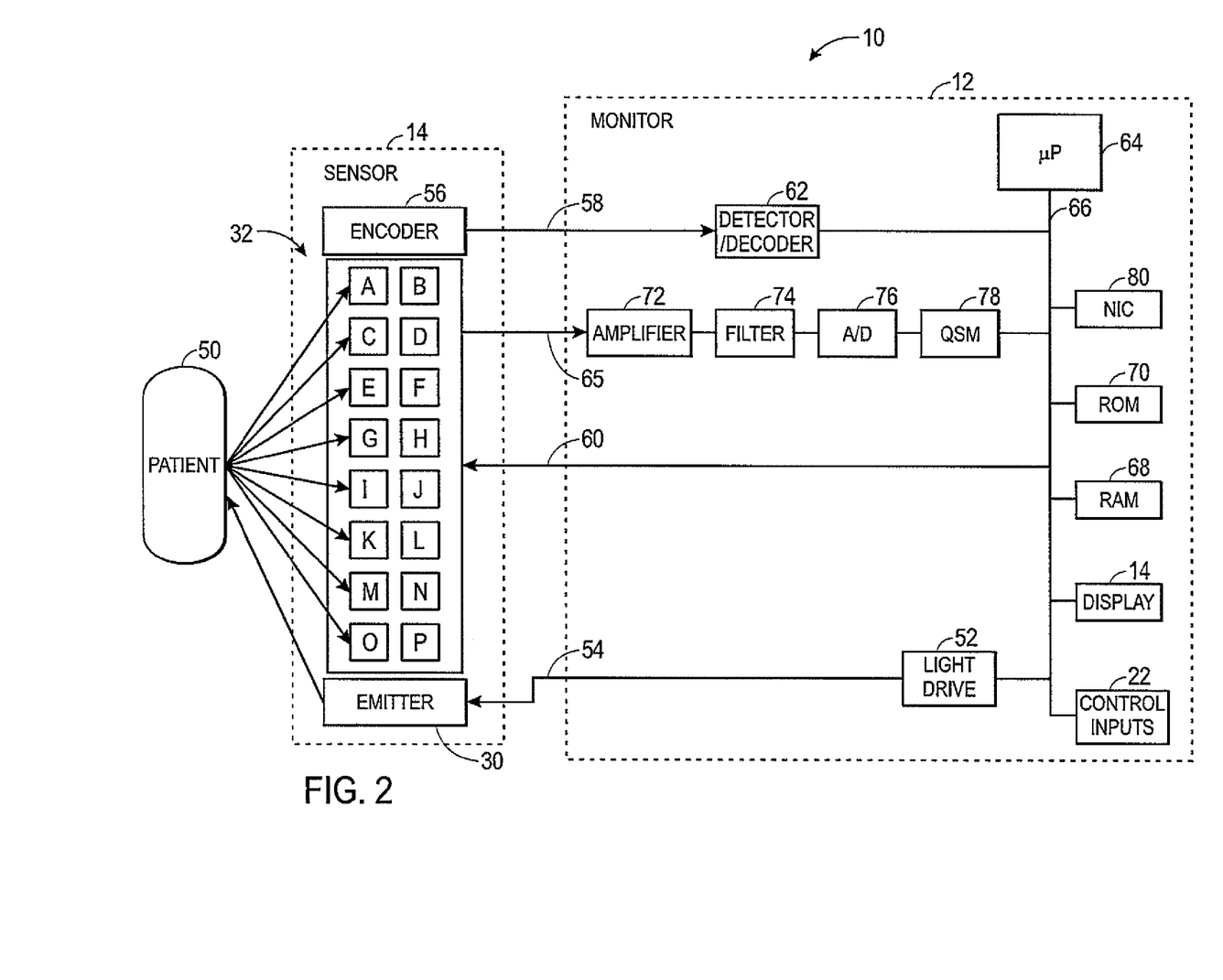
FIG. 2 illustrates a simplified block diagram of a pulse oximeter having a filtered detector array, in accordance with an embodiment of the present disclosure.

The emitter 30 is generally capable of emitting multiple wavelengths of light, either through the use of multiple LEDs or a broadband source. For example, an emitter 30 for a pulse oximetry sensor 14 may include two LEDs: one LED emitting RED light (e.g., wavelength between about 600 to 700 nm), the other LED emitting infrared (IR) light (e.g., wavelength between about 800 to 1000 nm). In another embodiment, the emitter 30 may include a broadband source, such as an incandescent bulb or a phosphor-modified LED, which may be capable of emitting a plurality of wavelengths (e.g., from about 600 nm to about 1000 nm). The illustrated emitter 30 is controlled by the light drive 52 of the monitor 12 via the emitter line 54. In another embodiment, the light may alternatively be produced by the light drive 52 inside the monitor 12 and subsequently transmitted to the emitter 30, for example, using one or more fiber-optic cables as the emitter line 54.

Additionally, the sensor 14 may include encoder 56 containing encoded information about the sensor 14. For example, such information may include the sensor type (e.g., whether the sensor is intended for placement on a forehead, digit, earlobe, etc.), the number and organization of detector array 32 and emitters 30 present on the sensor 14, the wavelengths of light emitted by the emitter 30, and/or calibration coefficients or calibration curve data to be used in the calculation of the physiological parameter. The information provided by the encoder 56 may be supplied to the monitor 12 (e.g., via the encoder signal line 58) and may indicate to the monitor 12 how to interface with and control the operation of sensor 14, as well as how data is to be exchanged and interpreted. For example, the encoder 56 may supply the monitor 12 with information regarding the control and data lines (e.g. lines 54, 60, or 65) between the monitor 12 and the sensor 14, in addition to the types and ranges of signals that may be transmitted via these communication lines during operation of the system 10. The encoder 56 may also, for example, indicate to the monitor 12 that the sensor 14 has a detector array 32 as well as indicate how to use the control line 60 to select particular photodetector signals from detector array 32. The encoder 56 may also provide information to allow the monitor 12 to select appropriate algorithms and/or calibration coefficients for calculating the physiological characteristics of the patient 50. In certain embodiments, the encoder 56 may, for instance, be implemented as a memory on which the described sensor information may be stored. In one embodiment, the data or signal from the encoder 56 may be decoded by a detector/decoder 62 in the monitor 12, and the detector/decoder 62 may be coupled to the processor 64 via the internal bus 66 of the monitor 12.

In the depicted embodiment of FIG. 2, the sensor 14 possesses a filtered detector array 32 having portions of the array configured to certain types of light (e.g., based on wavelength and/or polarization) and convert the received light to an electrical signal. In operation, light enters a photodetector (e.g., any of 32A-P) after traversing the tissue of the patient 50 and one or more filters, as described in detail below. In general, a photodetector (e.g., any of 32A-P) may convert light at a given intensity, which is generally related to the absorbance and/or reflectance of the light in the tissue of the patient 50, into an electrical signal. In certain embodiments, the detector array 32 may include one or more CCD detector elements, similar to those used in digital photography. In other embodiments, the detector array 32 may include one or more CMOS detector elements, similar to those used in optical communication applications. Furthermore, in certain embodiments, the individual photodetectors in the photodetector array may be manufactured having a center-to-center distance typically less than 1 μm. In certain embodiments, the center-to-center distance may be as great as 100 μm or more.

Each of the lines coupling the patient monitor 12 to the patient sensor 14 in the illustrated embodiment may represent one or more channels, wires, or cables. In some embodiments, the illustrated lines (e.g., lines 58, 65, 60, and 54) may be bundled together into a single cable (e.g., cable 28) coupling the sensor 14 to the monitor 12. As such, each photodetector 32A-P in the detector array 32 may have its own channel or dedicated wire in the signal input line 65 to the patient monitor 12. Alternatively, each photodetector 32A-P may be connected to a multiplexor (e.g., built into the detector 32), whose output is, in turn, coupled to a single channel or wire of the signal input line 65 to the monitor 12. Accordingly, the patient monitor 12 may provide control signals over one or more channels or cables in the control line 60 to control the operation of the detector array 32 (e.g., send the signal of a certain photodetector or group of photodetectors in the photodetector array 32 to the monitor 12 via the signal input line 65). For example, patient monitoring system 10 may include a multiplexed detector array having elements and features described in detail in U.S. patent application Ser. No. 13/077,105, filed Mar. 31, 2011, entitled "MULTIPLEXED PHOTODETECTOR ARRAY FOR OPTICAL MEDICAL SENSORS," which is incorporated by reference herein in its entirety for all purposes.

The patient monitor 12 may include one or more processors 64 coupled to an internal bus 66 and generally controlling the operations of the patient monitoring system 10. For example, the processor 64 may control the detector array 32 of the patient sensor via the internal bus 66 and control line 60. The illustrated monitor 12 includes random access memory (RAM) 68, read only memory (ROM) 70, control inputs 22, and a display 14 attached to the internal bus 66. In the illustrated embodiment, the signal received from the sensor 14, via signal input line 65, is subsequently passed through an amplifier 72, a low pass filter 74, and an analog-to-digital converter 76 to amplify, filter, and digitize the electrical signals, respectively. The digital signal data may then be stored in a queued serial module (QSM) 78, for later downloading to RAM 68 as the QSM 78 fills up. In other embodiments, there may be multiple parallel paths for separate amplifiers, filters, and A/D converters for multiple light wavelengths or spectra received by different photodetectors 32A-P. The control inputs 22 may also be coupled to the internal bus 66 of the monitor 12 such that monitor parameters set or adjusted using the control inputs 22 may be applied in the operation of the patient monitoring system 10. Additionally, some embodiments of the monitor 12 may also include a network interface card 80, wired or wireless, that may interface with the internal bus 66 of the monitor 12 and allow the transmission of data and/or control signals between a computer network and the monitor 12.

In an embodiment, based at least in part upon the received signals corresponding to the light received by the detector array 32, the processor 64 may calculate, for example, the oxygen saturation of the patient 104 using various algorithms. These algorithms may use particular coefficients, which may be empirically determined and stored on the sensor 14 or monitor 12. For example, algorithms relating to the distance between the emitter 30 and each photodetector (e.g., 32A-P) may be stored in the monitor (e.g., in ROM 70) or in the sensor (e.g., in the encoder 56) and accessed and operated according to the instructions of the processor 64.

Figure 3:
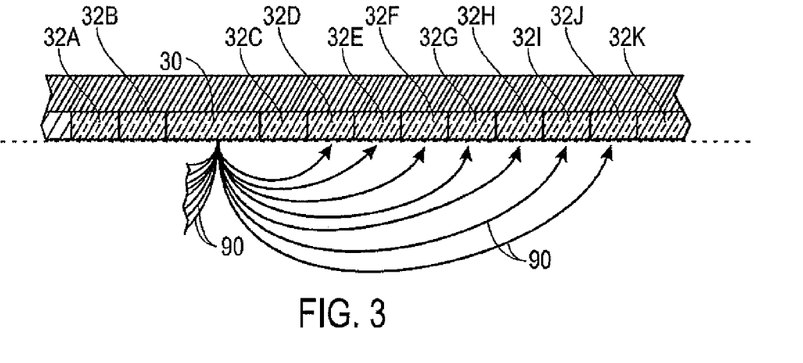
FIG. 3 illustrates a side-view of a filtered detector array in contact with the tissue of a patient during operation, in accordance with an embodiment of the present disclose.

In general, pulse oximetery sensors typically operate to measure light that has either been transmitted through the tissue of the patient (i.e. transmission mode) or light that has been reflected by the tissue of the patient (i.e. reflectance mode). When affixed to a patient, the sensor 14 may employ a reflectance-type measurement to determine one or more physiological characterizes of a patient. For example, FIG. 3 illustrates a portion of a reflectance-type sensor 14 in contact with the tissue of a patient 50. In the illustrated embodiment, the emitter 30 is positioned adjacent to the photodetectors (e.g., 32A-K) such that light passes through the patient 50 via one or more light paths 90. The light paths 90 may, for example, begin at emitter 30 and end at photodetector elements 32D-J, respectively. By exploiting particular light paths 90 having particular tissue depths, a sensor 14 may be adapted for use with an infant (e.g., using relatively shallow light paths 90) or an adult (e.g., using relatively deeper light paths 90). Furthermore, as discussed in detail below, one or more filters may be disposed over each photodetector (e.g., 32A-K) in the photodetector array 32 such that each photodetector only measures light having particular properties (e.g., particular wavelengths and/or polarizations). In certain embodiments, the same filters may be disposed over certain portions of the detector array (e.g., photodetectors 32A, 32D, 32G) such that these portions of the detector array 32 are configured to measure light having similar properties, but traversing a different light path 90.

Generally speaking, the light path 90 ending at location 32D is shorter than the light path 90 ending at location 32G, which is shorter than the light path 90 ending at location 32J. Additionally, the light path 90 ending at location 32D follows a shallower route than the light path 90 ending at location 32G, which is shallower than the light path 90 ending at location 32J. Light paths 90 that pass through the tissue of the patient 50 at different depths and having different lengths may be advantageous for scanning and selecting signals from the detector array 32 at certain locations on the patient 50. That is, if, for example, bone or other tissue interferes with the light path 90 to a given location (e.g., 32D) such that a given photodetector element (e.g., 32D) may not receive sufficient light to generate an adequate electrical signal for further computation, the processor 64 may scan the detector array 32 for signals from other locations (e.g., photodetectors 32G and/or 32J), which may be used by the processor 64 to calculate the physiological parameters of the patient 50.

By further example, a light path 90 leading to a particular detector (e.g., 32G) traverses relatively large vasculature (e.g., vein or artery) near the surface of the tissue of the patient 50. Accordingly, the measurement of a photodetector (e.g., 32G) receiving light from this light path 90 may be skewed relative to other photodetectors in the detector array 32 that are configured to measure the same type of light. Accordingly, in certain embodiments, the processor 64 may collect and discard the skewed signal measurement and rely instead upon signals measured by similarly filtered portions of the photodetector array 32 to calculate the physiological parameter of the patient 50. By specific example, in certain embodiments, the processor 64 may collect the output signals from a portion of the photodetectors in the detector array 32 (e.g., photodetectors 32A, 32D, and 32G) that are configured to measure the same type of light, and the processor 64 may use these output signals to determine an average output signal for the portion of the photodetectors in the detector array 32. Then, the processor 64 may discard one or more of the output signals of the portion of the photodetectors in the detector array 32 that differ from the average output signal by more than a threshold value. In other embodiments, the processor 64 may average the signals measured by similarly filtered portions of the detector array 32 such that the effects of the local vasculature on the calculation of the patient's physiological parameter may be mitigated.

As mentioned above, utilizing a filtered detector array enables the use of a broadband light source as the emitter 30. Accordingly, in certain embodiments, the sensor 14 may include a phosphor-modified LED as a broadband emitter 30. One advantage to using a phosphor-modified LED over an array of narrowband LEDs is that a single phosphor-modified LED may be configured to emit over a broad range of wavelengths, including wavelength ranges for which individual narrowband LEDs are not readily available or cost effective.

Figure 4:
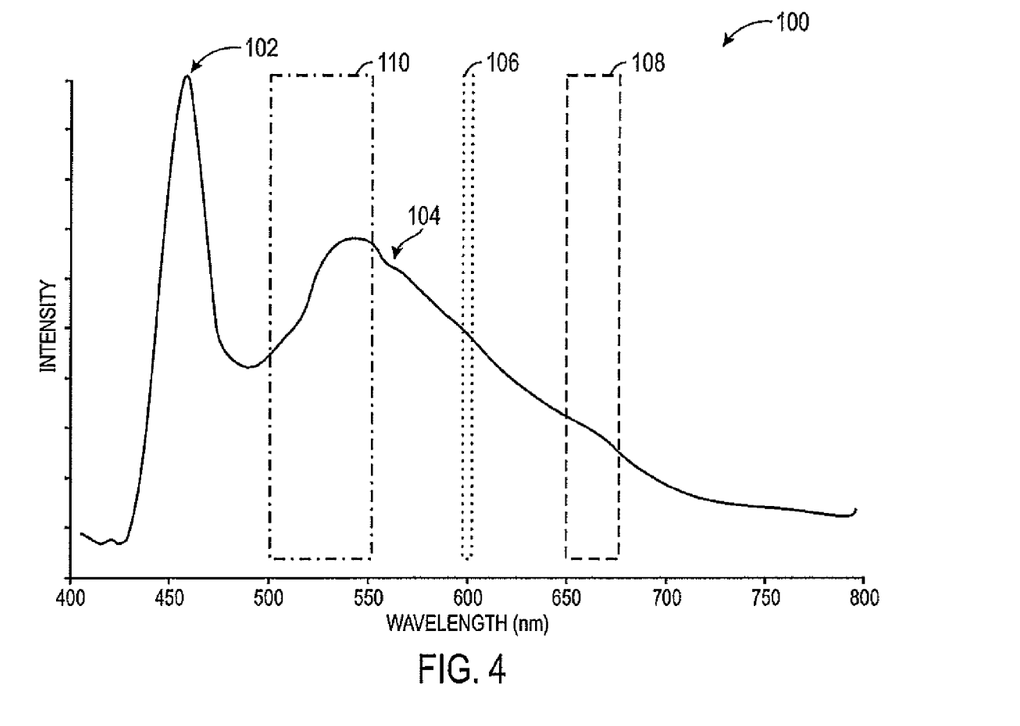
FIG. 4 is a graph illustrating the spectrum of a broadband emitter and different detector windows of various filters, in accordance with an embodiment of the present disclose.

An example of the emission of a phosphor-modified LED is illustrated in graph 100 of FIG. 4. In the illustrated graph 100, an initial emission peak 102 is observed (at approximately 460 nm) that has the greatest intensity. For a phosphor-modified LED, the LED emission peak 102 corresponds to the relatively narrow-band emission of the LED component of the emitter 30. The broader peak to the right of the LED emission peak 102 is the phosphor emission peak 104. That is, the phosphor component of the phosphor-modified LED emitter 30 is generally a material that absorbs a portion of the light emitted by the LED (e.g., at approximately 460 nm) and emits light over a broad range of wavelengths (e.g., between 480 and 800 nm). Accordingly, graph 100 illustrates the emission of both the LED and the phosphor components of the phosphor-modified LED in order to produce light over a broad spectrum (e.g., from approximately 440 nm to 800 nm). It should be appreciated that any number of LEDs could be combined together with a phosphor component to produce almost any desired spectrum. Alternatively, even an incandescent bulb may be used as a broadband emitter, should the source spectrum be more suitable than an LED based source.

However, not all wavelengths of light produced by a broadband source are measured by the sensor 14 to determine the physiological parameters of the patient 50. That is, a photodetector (e.g., any of 32A-K) in the detector array 32 may be filtered to only receive and measure light of a particular range of wavelengths (i.e., the detection window) from the spectrum produced by the emitter 30. In certain embodiments, reflective or absorptive filters may be disposed over portions of the detector array 32. Generally speaking, reflective filters, such as dielectric stack filters or dielectric mirrors, reflect light having undesirable wavelengths and/or polarizations and allow only light having particular wavelengths and/or polarizations to pass. In contrast, absorptive filters, including the Red, Green, and Blue (RGB) filters used in liquid crystal displays (LCDs) and certain filters based on organic dyes, absorb light having undesirable wavelengths and/or polarizations and allow only light having particular wavelengths and/or polarizations to pass. In certain embodiments, the reflective or absorptive filter may be dichromatic, meaning that two particular wavelength ranges (e.g., 650-700 nm and 900-1000 nm) may traverse the filter while the remaining wavelengths are reflected or absorbed.

Accordingly, the light detection behavior of each photodetector in the photodetector array 32 may be substantially defined by the properties of the filters. For example, the size of the detection window of a particular photodetector (e.g., any of 32A-K) may be defined by the properties of the one or more filters disposed over the photodetector. Certain types of filters may provide a narrower detection window than others, allowing only a very limited range of wavelengths to traverse the filter layer(s) to produce a signal at a particular photodetector. Some types of filters, such as dielectric stacks, may provide a relatively narrow window of wavelengths (e.g., approximately 2 nm-5 nm). For example, detector window 106 may represent the narrow detector window of a photodetector (e.g., any of 32A-K) having a dielectric stack filter. Other types of filters, such as RGB filters, may provide a broader detection window (e.g., approximately 20 nm-50 nm). For example, the illustrated detection window 108 may represent the detection window of a RGB filter where the window extends from approximately 650 nm to 675 nm. By further example, the illustrated detection window 110 may represent the detection window of a RGB filter extending between approximately 500 and 550 nm. Accordingly, in certain embodiments, different portions of the detector array 32 (e.g., particular photodetectors from 32A-K) may include either a dielectric stack filter or a RGB filter such that only the portions of the emission spectrum 100 falling within a detection window (e.g., 106, 108, or 110) may traverse the filters and produce a signal.

Figure 5:
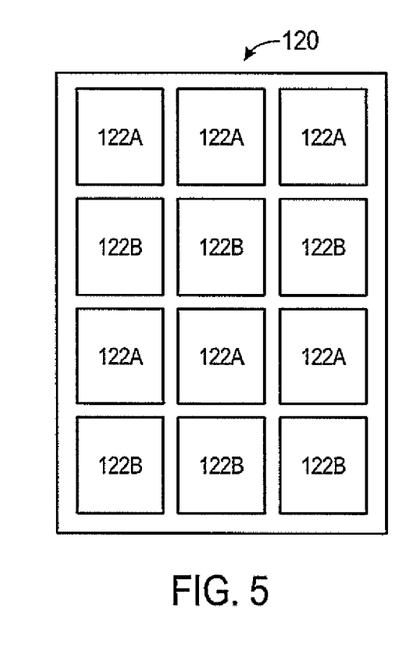
FIG. 5 illustrates a top-down view of a detector array having square-shaped filters, in accordance with an embodiment of the present disclosure.

The filters may be organized on the CCD or CMOS detector array 32 in a number of ways. In certain embodiments, each photodetector of the photodetector array may include an individual filter. For example, FIG. 5 illustrates a detector array 120 that includes three columns of photodetectors, each column containing four photodetectors. In other embodiments, the detector array may be arranged as linear array of 32 to 1024 photodetector elements or as a rectangular array of 64×64 photodetector elements. In certain embodiments, the detector array 120 may be implemented as an IC package having the filter layers disposed about the surface. In the embodiment illustrated in FIG. 5, square-shaped filters (e.g., 122A and 122B) are disposed over each photodetector in the photodetector array 120. Furthermore, in the illustrated embodiment, the two filters, 122A and 122B, are capable of detecting different wavelengths of light. For example, the first type of filter may be a RGB filter with a detection window from approximately 600 to 650 nm, which allows the photodetectors beneath filters 122A to detect only RED light. By further example, the second type of filter may also be a RGB filter with the detection window from approximately 900 nm to 950 nm, which allows the underlying photodetectors (e.g., 32D-F and 32J-L) to detect only IR light. Accordingly, in certain pulse oximetry sensor 14 embodiments, such a detector array 120 may be used to measure both RED and IR light from the tissue of the patient 50 along various light paths 90 such that the oxygen saturation (e.g., $SpO_2$) of the patient 50 may be determined. As described above, by using multiple portions of the detector array 32 to measure light of the same wavelength (e.g., RED or IR) signal artifacts introduced by vasculature, bone tissue, or other localized distortions may be mitigated. Additionally, since the selectivity of the sensor relies upon the filters 122A and 122B, the sensor may use a single broadband source (e.g., a phosphor-modified LED) for the emitter 30 rather than multiple narrowband LEDs (e.g., a RED and an IR LED), potentially reducing the cost and the complexity of the sensor 14. While each row of photodetectors in the illustrated embodiment shares a common filter type (e.g., 122A or 122B), in other embodiments, the two filter types may be organized into random or checkerboard patterns. Furthermore, in other embodiments, instead of individual squares, each row of photodetectors may be disposed beneath a continuous filter strip to ease manufacturing difficulty and cost. Additionally, in certain embodiments, multiple layers of filters may be disposed over each photodetector in an arrangement similar to the one depicted in FIG. 5, as will be discussed in detail below.

Figure 6:
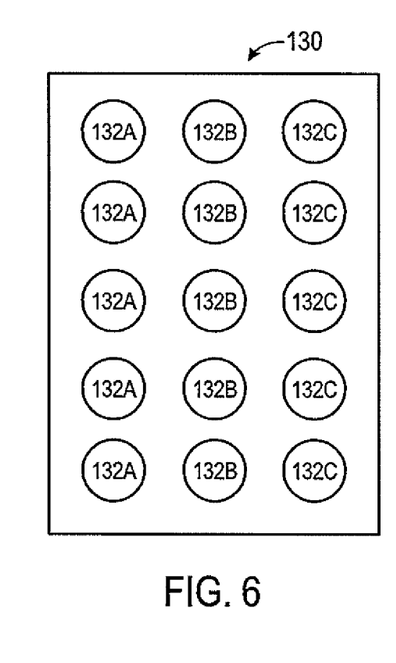
FIG. 6 illustrates a top-down view of another detector array having circular filters, in accordance with an embodiment of the present disclosure.

In certain embodiments, the filter layers disposed on top of the photodetectors of the detector array may have a different shape. For example, FIG. 6 illustrates a detector array 130 including 5 rows and 3 columns of photodetectors, each disposed beneath one of three types of a circular filters: 132A, 132B, or 132C. In certain embodiments, such a detector array 130 may be used in a optical aquametry sensor 14 similar to those described in U.S. patent application Ser. No. 11/240,927, filed Sep. 30, 2005, entitled, "DEVICE AND METHOD FOR MONITORING BODY FLUID AND ELECTROLYTE DISORDERS," which is incorporated herein in its entirety for all purposes. Optical aquametry sensors generally determine the hydration of a patient by measuring two or three wavelengths of light from the irradiated tissue of the patient. In the illustrated detector array 130 embodiment, three types of filters are used: 132A is a dielectric stack filter having a detection window centered around 1710 nm, 132B is a dielectric stack filter having a detection window centered around 1730 nm, and 132C is a dielectric stack filter having a detection window centered around 1740 nm. While the illustrated detector array 130 only includes three types of filters, other patient hydration sensor embodiments may include 4 to 10 types of filters providing various detection windows over relevant wavelength ranges (e.g., 1100-1350 nm, 1500-1800 nm, and 2000-2300 nm). In certain embodiments, one or more of the photodetectors in the detector array 130 may be manufactured using any number of semiconductor materials, including Indium-Gallium-Arsenide, in order to detect light over a wavelength range of interest (e.g., 1500-1800 nm). As described above, since multiple portions of the detector array 130 measure light of the same wavelength, an aquametry sensor 14 utilizing such a detector array 130 affords a sensor that is robust to local distortions caused by variations in the tissue composition, sensor/patient contact issues, and/or individual photodetector failures. Furthermore, as described above, utilizing a filtered detector array 130 enables a sensor to use either a broadband light source or one or more narrowband light sources as the emitter 30, which may afford benefits in terms of the sensor cost and/or difficulty of manufacturing.

Figure 7:
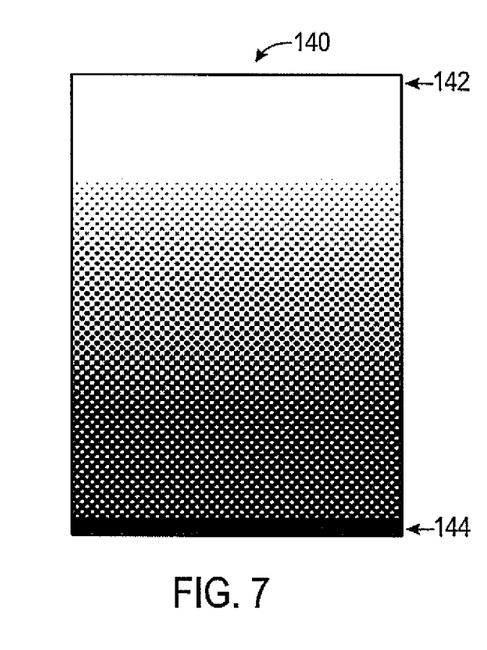
FIG. 7 illustrates a top-down view of a single, continuous, graded filter, in accordance with an embodiment of the present disclosure.

Furthermore, in certain sensor embodiments, a single continuous gradient filter may be disposed over the entire detector array. That is, the use of a single, continuous filter may ease manufacturing difficulty and cost compared to the multi-segmented filters described above with respect to FIGS. 5 and 6. For example, FIG. 7 illustrates a gradient polarization filter 140 in which a greater portion of light having certain polarizations is allowed to traverse the top 142 of the filter compared to the bottom 144 of the filter. That is, the bottom 144 of the filter 140 may only allow light having a particular polarization to pass, while the top 142 of the filter may allow light having any polarization to pass. For example, a pulse oximetry sensor utilizing such a detector array 140 may emit light of a particular polarization into the tissue of a patient. Light that interacts with the tissue of the patient tends to change in polarization. However, detected light having the same polarization as was emitted into the tissue of the patient may be the result of reflection from the surface of the patient's tissue (e.g., due to poor patient/sensor contact). As such, it may be beneficial to have a portion of the detector (e.g., the portion of the detector that is closest to the emitter) filter out a greater degree of light having the same polarization as was emitted into the patient's tissue so that photodetectors beneath this portion of the detector array measure little to no reflected light.

Figure 8:
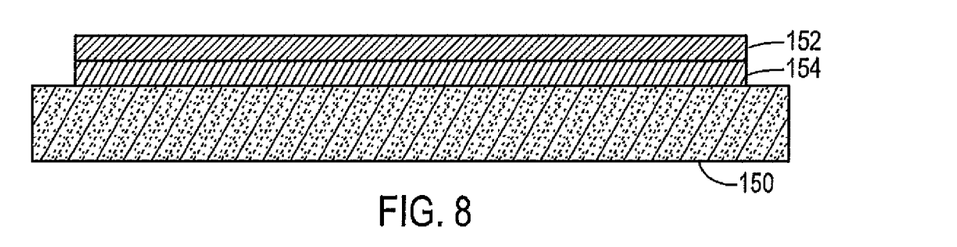
FIG. 8 illustrates a side-view of a photodetector having multiple filter layers, in accordance with an embodiment of the present disclosure.

Additionally, in certain embodiments it may be desirable to use multiple layers of filters over each photodetector. For example, it may be desirable to measure light having both a particular wavelength and polarization. Accordingly, FIG. 8 illustrates a side view of a photodetector 150 of a photodetector array 32 that is disposed beneath two filter layers, namely filters 152 and 154. In the illustrated embodiment, filter layer 152 is a non-graded polarization filter, similar to the polarization filters used in certain sunglasses, which evenly filters out light having the same polarization as the emitter 30. Filter layer 154 of the illustrated embodiment is an RGB filter having a detection window between approximately 600 and 650 nm, allowing only RED light to pass. Accordingly, the illustrated photodetector 150 is configured to only receive RED light having a polarization other than the polarization of the light emitted into the tissue. In other embodiments, more than two layers of filters may be disposed on over each photodetector.

Figure 10:
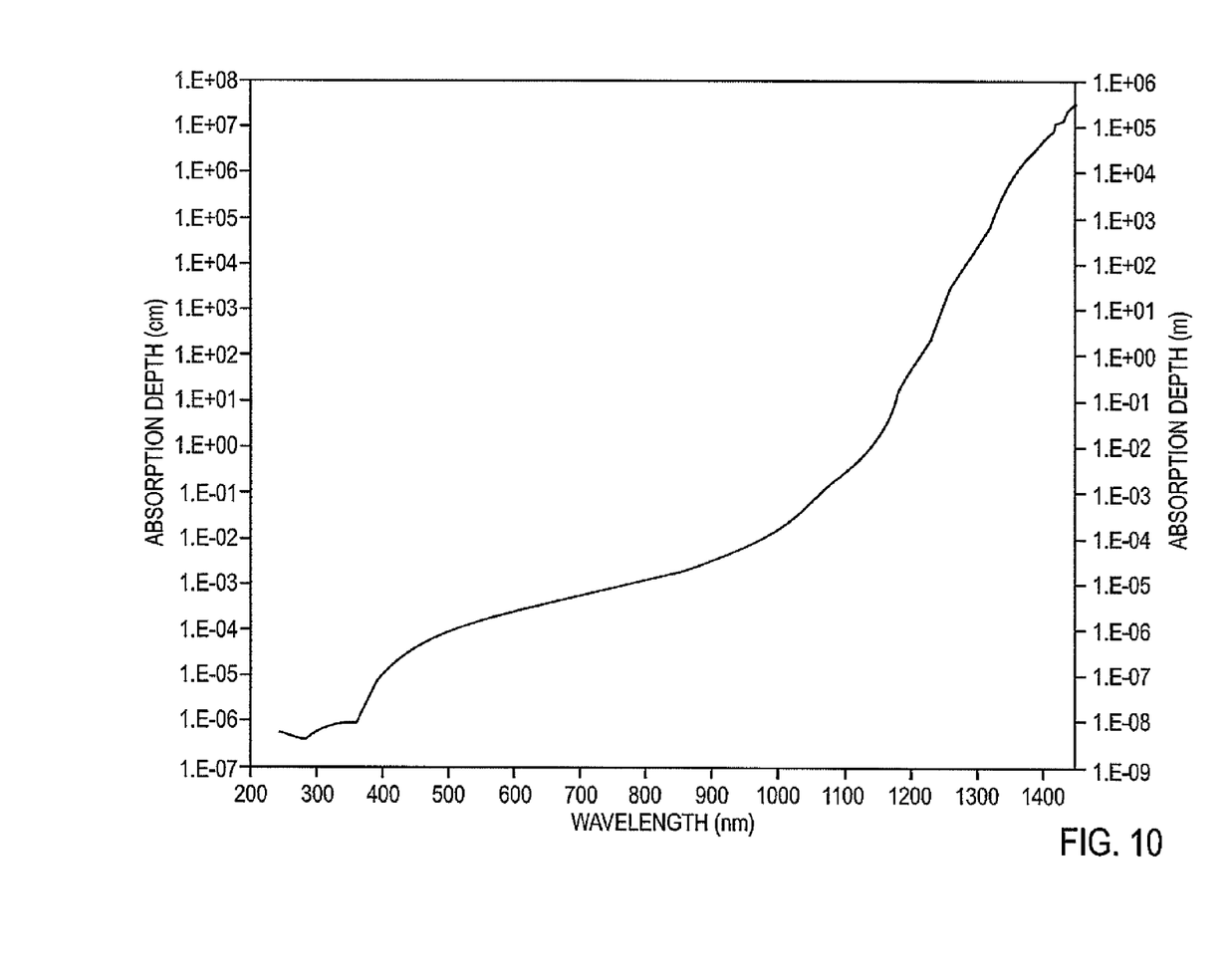
FIG. 10 is a graph illustrating absorption depth (cm) versus wavelength (nm) for silicon, in accordance with an embodiment of the present disclosure.

Furthermore, certain optical sensor embodiments may include photodetectors having multiple photodetection layers. That is, each photodetector may include two or more photodetection layers configured to detect different wavelengths of light. Since each photodetector element in such a structure is capable of measuring more than one wavelength of light, fewer photodetectors may be used in the photodetector array to measure the same number of wavelengths of light, potentially reducing the manufacturing cost. In certain embodiments, this may be accomplished by exploiting the optical properties of the substrate (e.g., silicon) such that only light of a particular wavelength, or a particular wavelength range, may reach and produce a signal within a particular photodetection layer. As generally illustrated in FIG. 10, silicon has an absorption depth that varies with wavelength. As such, the shallow depths of a silicon-based photodetector may be used to detect shorter wavelengths (e.g., 400-700 nm), whereas deeper layers of the photodetector may be used to detect longer wavelengths of light (e.g., 800-1000 nm). Additionally, each photodetector in the detector array may be constructed using silicon having slightly different optical properties due to different levels of doping (e.g., n-doping or p-doping) such that a plurality of different wavelengths may be detected without separate filter layers. Similar approaches have been applied to CMOS detectors for photodetectors, such as the Foveon X3® direct image sensor manufactured by Sigma Photo™ and described in U.S. Pat. No. 5,965,875. In certain pulse oximetry sensor embodiments, a detector array may include a plurality of photodetectors having two photodetection layers that detect two different wavelengths of light (e.g., RED and IR light). Additionally, in certain patient hydration sensor embodiments, a detector array may include a plurality of photodetectors having three to five photodetection layers configured to detect five different wavelengths of light (e.g., around 1200 nm, 1300 nm, 1710 nm, 1730 nm, and 1740 nm).

Figure 9:
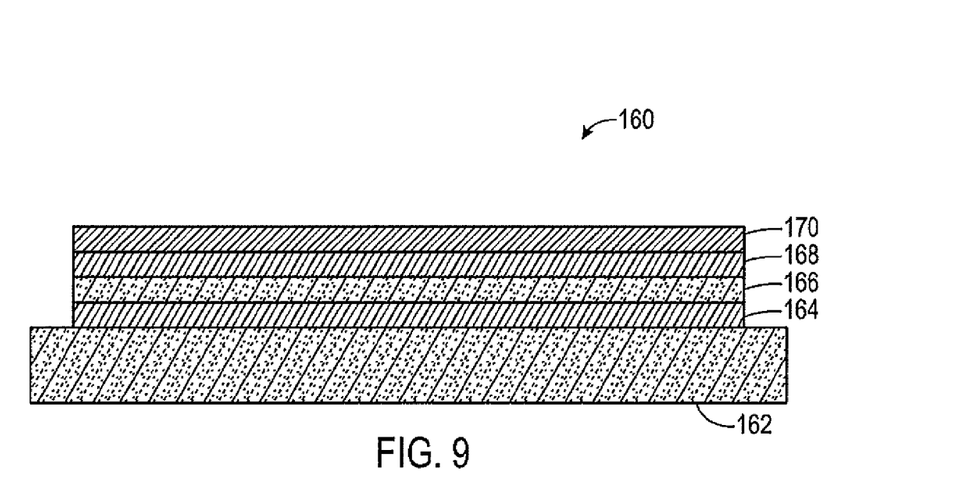
FIG. 9 illustrates a side-view of a photodetector having multiple filter and detection layers, in accordance with an embodiment of the present disclosure.

However, in other detector array embodiments, a filter layer may be disposed over each photodetection layer. For example, turning to FIG. 9, a side view of a photodetector 160 having both filter layers and multiple detection layers. In the illustrated photodetector embodiment, the bottom layer 162 is a photodetector layer similar to the photodetection layer 150 illustrated in FIG. 8. Disposed on top of the bottom layer 162 is a dielectric stack filter layer 164, which affords a detection window centered around 650 nm for the underlying detection layer 162. Disposed on top of the dielectric stack filter layer 164 is a second detection layer 166. Unlike the bottom detection layer 162, the upper detection layer 166 is substantially transparent to certain wavelengths of light (e.g., RED light). On top of the upper detection layer 166 in the illustrated embodiment, a dichromatic filter may be disposed, which allows light of two different wavelength ranges to pass to the underlying upper detection layer 166. Finally, the top layer of the illustrated photodetector 160 is a polarization filter similar to the polarization filter 152 of FIG. 8. In other embodiments, similar filtering and detection may be implemented using the varying absorption-depths of different semiconductor materials used for constructing the photodetectors.

For a sensor embodiment utilizing such a photodetector 160, a broadband light source may be used to emit light of a particular polarization into the tissue of a patient. Subsequently, after traversing the tissue of the patient, the light from the emitter may arrive at the top layer 170 of the structure illustrated in FIG. 9. The top polarization filter layer 170 reflects all light having the same polarization as the light source and allows all other polarizations of light to pass. Subsequently, the light reaches the dichromatic filter layer 168, where only RED and IR light are allowed to pass and all other wavelengths of light are absorbed. Then, the light may reach the upper detection layer 166, which may measure a signal for the combined RED and IR light. After traversing the upper detection layer 166, the remaining RED and IR light arrives at the dielectric stack filter layer 164, which only allows a narrow range of wavelengths of RED light to reach the bottom detection layer 162. Accordingly, the processor 64 of the monitor 12 may subtract a portion of the detector signal from the bottom detection layer 162 (e.g., the RED signal) from a portion of the detector signal from the upper detection layer 166 (e.g., the combined RED and IR signal) to determine measurements for both RED and IR light received by the photodetector 160.

Accordingly, through the use of filtered detector arrays, the disclosed embodiments enable the use of broadband light sources while still maintaining a high level of wavelengths selectivity when measuring the light returning from the tissue of the patient. Furthermore, the disclosed filtered detector array embodiments enable the precise selection of the polarization and/or the wavelength of the light that reaches the detection layer to produce a signal, which may enable the removal of certain artifacts prior to performing the measurement. Additionally, the disclosed filtered detector array may provide a robust sensor for dealing with local tissue irregularities, sensor/patient contact issues, and/or individual photodetector failure. Furthermore, the disclosed embodiments afford an improved solution over the use of costly and bulky spectrometers in patient sensors.

What is claimed is:

1. A physiological sensor, comprising:
an emitter configured to emit two or more wavelengths of light having a first polarization into the tissue of a patient;
a charge coupled device (CCD) or complementary metal-oxide semiconductor (CMOS) photodetector array comprising a plurality of photodetectors, wherein each photodetector is configured to receive the light from the tissue of the patient and to produce a corresponding output signal; and
one or more filter layers disposed over the plurality of photodetectors, wherein a first portion of the one or more filter layers is configured to only allow light associated with a first physiological measurement to reach a first portion of the plurality of photodetectors, wherein a second portion of the one or more filter layers is configured to only allow light corresponding to a second physiological measurement to reach a second portion of the plurality of photodetectors, and wherein the one or more filter layers comprise a graded polarization filter layer configured to block a greater amount of light of the first polarization from reaching a portion of photodetector array disposed nearest the emitter.

2. The sensor of claim 1, wherein the emitter comprises a broadband, phosphor-modified LED emitter.

3. The sensor of claim 1, wherein the photodetector array comprises a linear CMOS photodetector array.

4. The sensor of claim 1, wherein the one or more filter layers comprise a dielectric stack filter layer.

5. The sensor of claim 1, wherein the one or more filter layers comprise an RGB filter layer.

6. The sensor of claim 1, wherein at least two of the plurality of photodetectors are disposed under the same one or more filter layers.

7. The sensor of claim 1, wherein the first physiological measurement is an oxygen saturation ($SpO_2$) or a pulse rate measurement of the patient.

8. The sensor of claim 7, wherein the first portion of the one or more filter layers is configured to only allow light having wavelengths between 600 nm and 700 nm, between 800 nm and 1000 nm, or a combination thereof, to reach the first portion of the plurality of photodetectors.

9. The sensor of claim 1, wherein the second physiological measurement is a hematocrit measurement or a hydration measurement of the patient.

10. The sensor of claim 9, wherein the second portion of the one or more filter layers is configured to only allow light having wavelengths between 1100 nm and 1350 nm, or between 1500 nm and 1800 nm, or between 2000 nm and 2300 nm, or a combination thereof, to reach the second portion of the plurality of photodetectors.

11. The sensor of claim 1, wherein the graded polarization filter layer is configured to limit reflected light reaching the photodetectors disposed nearest the emitter.

12. A method of measuring a physiological parameter of a patient comprising:
    emitting light into a tissue of the patient using a broadband emitter;
    filtering the light received from the tissue of the patient using a graded polarization filter layer and one or more multi-segmented filter layers, wherein each segment of the multi-segmented filter layers is configured to block a different portion of the light based on either the wavelength of the light, the polarization of the light, or both, and wherein a portion of the graded polarization filter layer disposed nearest the broadband emitter is configured to block a greater amount of the light having a first polarization; and
    measuring the light that traverses the graded polarization filter layer and the one or more multi-segmented filter layers using a charge-coupled device (CCD) or complementary metal-oxide semiconductor (CMOS) detector array comprising a plurality of photodetectors.

13. The method of claim 12, wherein emitting light comprises emitting light into the tissue of the patient using a phosphor-modified LED emitter.

14. The method of claim 12, wherein each photodetector of the plurality of photodetectors comprises a plurality of photodetection layers, and wherein each of the plurality of photodetection layers is configured to measure a different portion of the light that traverses the one or more filters.

15. A patient monitoring system comprising:
an optical patient sensor comprising:
    a broadband emitter configured to emit light over a range of wavelengths and having a first polarization into the tissue of a patient;
    a first plurality of photodetectors disposed below a graded polarization filter layer and a first filter layer, wherein the first plurality of photodetectors is configured to receive a first filtered portion of the light traversing the tissue of the patient, the graded polarization filter layer, and the first filter layer, and configured to produce a corresponding first plurality of output signals; and
    a second plurality of photodetectors disposed below the graded polarization filter layer and a second filter layer, wherein the second plurality of photodetectors is configured to receive a second filtered portion of the light traversing the tissue of the patient, the graded polarization filter layer, and the second filter layer, and configured to produce a corresponding second plurality of output signals, wherein the graded polarization filter layer is configured to filter a greater amount of light having the first polarization from reaching a portion of the first or second plurality of photodetectors positioned nearest the broadband emitter; and
a patient monitor comprising a processor configured to:
    receive the first and second pluralities of output signals from the first and second pluralities photodetectors;
    calculate a first physiological parameter of the patient based, at least in part, on the received first plurality of output signals; and
    calculate a second physiological parameter of the patient based, at least in part, on the received second plurality of output signals.

16. The system of claim 15, wherein a first portion of the plurality of photodetectors is configured to receive a different filtered portion of the light from the tissue of the patient than a second portion of the plurality of photodetectors.

17. The system of claim 16, wherein the processor is configured to:
    compare a portion of the first plurality of output signals;
    discard one or more of the portion of the first plurality of output signals that differ from an average output signal by more than a threshold value.

18. The system of claim 15, wherein the first filter layer or the second filter layer comprise a multi-segmented filter or a RGB filter.

* * * * *